United States Patent [19]

Sinharay et al.

[11] 4,277,493

[45] Jul. 7, 1981

[54] SUBSTITUTED N¹-VINYL-N¹-METHYL-N²-ARYL-FORMAMIDINES AND THEIR USE AS PESTICIDES

[75] Inventors: Akhileswar Sinharay; Gerhard Stähler, both of Frankfurt am Main; Werner Bonin, Kelkheim, all of Fed. Rep. of Germany

[73] Assignee: Hoechst Aktiengesellschaft, Frankfurt am Main, Fed. Rep. of Germany

[21] Appl. No.: 123,279

[22] Filed: Feb. 21, 1980

[30] Foreign Application Priority Data

Feb. 23, 1979 [DE] Fed. Rep. of Germany ....... 2907090
Nov. 10, 1979 [DE] Fed. Rep. of Germany ....... 2945460

[51] Int. Cl.³ .................. A01N 37/52; C07C 121/84; C07C 123/00
[52] U.S. Cl. .................. 424/304; 260/465 D; 560/35; 424/309
[58] Field of Search .................. 260/465 D; 560/35; 424/304, 309

[56] References Cited

U.S. PATENT DOCUMENTS

| | | | |
|---|---|---|---|
| 3,898,270 | 8/1975 | Saito et al. | 560/35 |
| 4,076,837 | 2/1978 | Boger et al. | 424/304 |

*Primary Examiner*—Dolph H. Torrence
*Attorney, Agent, or Firm*—Curtis, Morris & Safford

[57] ABSTRACT

Compounds of the formula

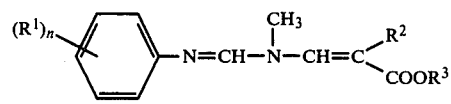

in which $R^1$ is halogen, alkyl, alkoxy, alkylthio, $CF_3$, $NO_2$, $CN_2$, phenoxy, halophenoxy, phenylthio or halophenylthio, $R^2$ is CN or $COOR^3$, $R^3$ is alkyl, alkoxyalkyl or cycloalkyl and n is 0 to 3 are effective insecticides and acaricides and especially ectoparasiticides.

15 Claims, No Drawings

SUBSTITUTED N¹-VINYL-N¹-METHYL-N²-ARYL-FORMAMIDINES AND THEIR USE AS PESTICIDES

It is an object of the present invention to provide substituted N¹-vinyl-N¹-methyl-N²-aryl-formamidines of the formula I

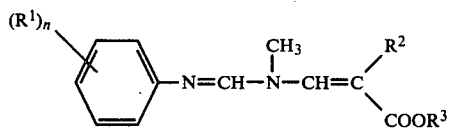

in which
n is zero or a number from 1 to 3,
R¹ is halogen, $(C_1-C_4)$-alkyl, $(C_1-C_4)$-alkoxy, $(C_1-C_4)$-alkylthio, trifluoromethyl, nitro, cyano, phenoxy, halophenoxy, phenylthio, or halophenylthio, in the case of n being 2 or 3 the radicals
R¹ possibly being identical or different,
R² is —CN or —COOR³ and
R³ is $(C_1-C_8)$-alkyl, $(C_1-C_8)$-alkoxyalkyl or $(C_3-C_6)$-cycloalkyl.

It is another object to provide a process for the manufacture of compounds of the formula I which comprises reacting N¹-methyl-N²-aryl-formamidines of the formula II

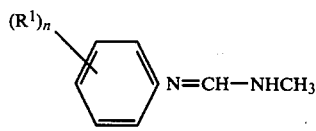

with cyanoacetic acid esters or malonic acid esters of the formula III

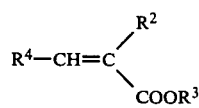

in which R⁴ is hydroxy, lower alkoxy or halogen, preferably chlorine.

N¹-Methyl-N²-aryl-formamidines of the formula II are known or can be produced by known methods (cf. U.S. Pat. Ser. No. 3,729,565).

Cyanoacetic acid esters and malonic acid esters of the formula III are also known or can be produced by known methods (cf. Bull. Soc. Chim. France, 25, pages 18 and 36 (1901); Annalen 297, page 75 (1897) and Chem. Berichte 103, page 1982 (1970)).

To produce the compounds of Formula I according to the invention the reaction components are preferably used in stoichiometric amounts. One of the components may also be used in an excess, for example up to 10%, but in general this does not involve any advantage. It proved advantageous to carry out the reaction in the presence of a solvent or diluent, for example inert polar or non polar solvents such as alcohols, for example methanol, ethanol, propanol, isopropanol, methoxyethanol; ketones, for example acetone, methylethylketone; ethers for example diethyl ether, diisopropyl ether, dibutyl ether, tetrahydrofurane, dioxane, dimethoxyethane; acetonitrile, benzene, toluene, xylene, chlorobenzene, methylene chloride, chloroform, ethyl acetate, cyclohexane, dimethyl formamide, dimethyl acetamide, or dimethyl sulfoxide.

The reaction temperatures are not critical and can be varied within wide limits, for example between −10° and +150° C., preferably between 20° and 120° C. In the case of alkoxymethylene cyanoacetic acid esters the reaction is preferably carried out at room temperature.

Depending on the temperature range chosen the reaction times are from several minutes to a few hours.

The process products, which are sparingly soluble in most solvents, are isolated by conventional methods, for example by suction filtration, by distilling off the solvent used or by diluting the reaction solution with water. If desired, the product can be purified by recrystallization from a suitable solvent mixture.

The compounds of the formula I present a novel class of compounds which have not yet been described in literature. They have valuable pesticidal, preferably insecticidal and acaricidal and especially ectoparaciticidal properties. They are, therefore, especially suitable for the control of acarina and preferably parasitic ixodidae. They combat all stadia of one-host and poly-host types of ticks and not only strains of normal sensitivity but also those that are resistant to phosphoric acid esters, carbamates and other compounds used for the control of ticks. The compounds of the invention strongly inhibit the fertility of the ticks and, moreover, they have a pronounced detaching effect which is especially important in the treatment of host animals infected with ticks (for example cattle). The detaching effect sets in immediately after application of the active substance in that the ticks are hindered to suck blood from the host. In the course of the treatment they fall off and the host animal is completely freed from the parasites.

Ticks that can be successfully combated by means of the compounds of the invention include, for example, types of the species Amblyomma, Aponomma, Boophilus, Dermacentor, Haemaphysalis, Hyalomma, Ixodes and Rhipicephalus.

It is, therefore, another object of the present invention to provide insecticidal and acaricidal and more especially ectoparasiticidal compositions which are characterized by a content of a compound of the formula I. The compositions are preferably commercialized in the form of emulsifiable concentrates which contain, besides the active substance or mixture of active substances, the usual formulation auxiliaries or additives, for example solvents, emulsifiers, wetting agents or dispersing agents, or in the form of wettable powders likewise containing, besides the active substance, the usual formulation auxiliaries or additives, for example wetting agents and dispersing agents, inert material, grinding auxiliaries and optionally penetration aids. In the compositions according to the invention the active substance content varies preferably from 2 to 95% by weight, more preferably from 10 to 60 % by weight. The compositions are advantageously used in the form of aqueous dilutions with which the animals or plants infested with the pest are treated by dabbing, spraying or dipping with the use of appropriate spraying decives or means or in appropriate installations. The dilutions used preferably have a content of active substance of 1 ppm to 5% by weight, more preferably 10 ppm to 0.5% by weight.

The following examples illustrate the invention.

(A) CHEMICAL EXAMPLES

EXAMPLE 1

$N^1$-(2-Ethoxycarbonyl-2-cyanovinyl)-$N^1$-methyl-$N^2$-(2,4-dimethylphenyl)-formamidine 48.6 g of $N^1$-methyl-$N^2$-(2,4-dimethylphenyl)-formamidine are dissolved in 100 cc of ether and a solution of 51 g of ethoxymethylene-cyanoacetic acid ethyl ester in 100 cc of ether is added at about 20° C. while stirring. The precipitated product is filtered off with suction after 5 hours. It is very pure. If desired it can be recrystallized from chloroform/petroleum ether (40°-80° C.). Yield 68 g, b.p. 140°-142° C.

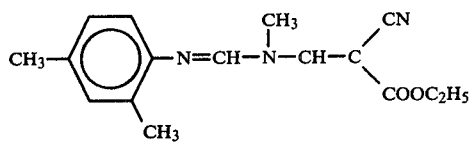

EXAMPLE 2

$N^1$-(2,2-Bis-ethoxycarbonylvinyl)-$N^2$-(2,4-di-methylphenyl)-$N^1$-methylformamidine 8.1 g of $N^1$-methyl-$N^2$-(2,4-dimethylphenyl)-formamidine, 12.9 g of ethoxymethylene-malonic acid diethyl ester and 50 cc of toluene are refluxed for 3 hours, the solvent is removed under reduced pressure and the residue is recrystallized from cyclohexane. Yield 3.1 g, m.p. 115°-116° C.

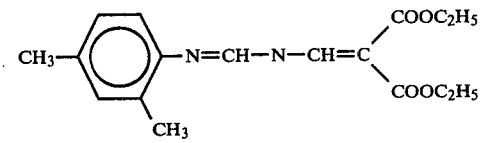

In analogous manner and with the use of corresponding starting components the compounds of the formula I listed in the following Tables 1 and 2 can be prepared.

TABLE 1

| Example No. | $(R^1)_n$ | $R^2$=CN $R^3$ | b.p. (°C.) |
|---|---|---|---|
| 3 | 2,6-$(CH_3)_2$ | —$C_2H_5$ | 140–141 |
| 4 | 3-Cl | " | 112–113 |
| 5 | 2,6-$(C_2H_5)_2$ | " | 100 |
| 6 | 2-$CH_3$, 4-Cl | " | 133–134 |
| 7 | 4-Cl | " | 140–141 |
| 8 | 2,4,6-$(CH_3)_3$ | " | 142–143 |
| 9 | 2,5-$(CH_3)_2$ | " | 130–131 |
| 10 | 2,3-$(CH_3)_2$ | " | 133–134 |
| 11 | 2-$CH_3$ | " | 120–121 |
| 12 | H | " | 115 |
| 13 | 2-$CF_3$, 4-Cl | " | 168 |
| 14 | 4-CN | " | 166–167 |
| 15 | 4-$NO_2$ | " | 157–158 |
| 16 | 4-$SCH_3$ | " | 128–129 |
| 17 | 4-$SC_6H_5$ | " |  |
| 18 | 4-O—⟨⟩—Cl (with Cl) | " |  |
| 19 | 3-Cl, 4-O—⟨⟩—Cl | " |  |

TABLE 1-continued

| Example No. | $(R^1)_n$ | $R^2$=CN $R^3$ | b.p. (°C.) |
|---|---|---|---|
| 20 | 3-Cl, 6-O—⟨⟩—Cl | " |  |
| 21 | 3-Cl, 4-F | " | 141 |
| 22 | 2-$CH(CH_3)_2$, 5-Cl | " |  |
| 23 | 2-$CH(CH_3)_2$, 4-Cl | " |  |
| 24 | 2-Cl, 3-$CF_3$, 4-F | " |  |
| 25 | 2,4-$Cl_2$ | " |  |
| 26 | 2,3-$Cl_2$ | " |  |
| 27 | 2,6-$Cl_2$ | " |  |
| 28 | 2-Cl, 4-$CH_3$ | " |  |
| 29 | 2-$OCH_3$, 4-$CH_3$ | " |  |
| 30 | 2-$CH_3$, 4-$OCH_3$ | " |  |
| 31 | 2,4-$(OCH_3)_2$ | " |  |
| 32 | 4-$OC_6H_5$ | " | 112–113 |
| 33 | 2,4-$(CH_3)_2$ | —$CH_3$ | 149 |
| 34 | 2,3-$(CH_3)_2$ | " |  |
| 35 | 2-$CH_3$ | " |  |
| 36 | 2,6-$(C_2H_5)_2$ | " |  |
| 37 | 2-$CH_3$, 4-Cl | " |  |
| 38 | 2,6-$[CH(CH_3)_2]_2$ | —$C_2H_5$ | 146–148 |
| 39 | 2,4-$(CH_3)_2$ | —$C_3H_7$ (i) | 120–121 |
| 40 | 2,4-$(CH_3)_2$ | —$C_4H_9$ (n) | 107–108 |
| 41 | 2,4-$(CH_3)_2$ | —$C_5H_{11}$ (n) | 79–81 |
| 42 | 2,4-$(CH_3)_2$ | —$C_2H_4OCH_3$ | 122–124 |
| 43 | 2,4-$(CH_3)_2$ | —⟨H⟩ | 130–131 |
| 44 | 2,4-$(CH_3)_2$ | —$C_4H_9$ (i) | 114–115 |
| 45 | 2,4-$(CH_3)_2$ | —$C_4H_9$ (tert.) |  |
| 46 | 2,4-$(CH_3)_2$ | —$C_8H_{17}$ (n) | 75–76 |
| 47 | 2,4-$(CH_3)_2$ | —⟨H⟩ | 120–121 |

TABLE 2

| Example No. | $(R^1)_n$ | $R^2$=$COOR^3$ $R^3$ | m.p. (°C.) |
|---|---|---|---|
| 48 | 2,3-$Cl_2$ | —$C_2H_5$ | 124–125 |
| 49 | 2,3$(CH_3)_2$ | " | 105–106 |
| 50 | 2,6-$(CH_3)_2$ | " | 90–91 |
| 51 | 4-Cl | " | 109–110 |
| 52 | 2,4,6-$(CH_3)_3$ | " | 98–99 |
| 53 | H | " | 110–111 |
| 54 | 4-$NO_2$ | " | 144–145 |
| 55 | 4-Cl, 2-$CF_3$ | " | 105–106 |
| 56 | 4-Cl, 2-$CH_3$ | " | 112–114 |
| 57 | 3-Cl, 4-F | " | 100–102 |
| 58 | 2-$CH_3$ | " | 96–97 |
| 59 | 2,6-(—CH—$CH_3$)$_2$ $CH_3$ | " | 158–159 |
| 60 | 2,4-$Cl_2$ | " | 87–88 |
| 61 | 2-CH, 3-Cl | " | 111–112 |
| 62 | 3-Cl | " |  |
| 63 | 2,5-$(CH_3)_2$ | " |  |
| 64 | 4-CN | " |  |
| 65 | 4-$SCH_3$ | " |  |
| 66 | 4-Br | " |  |
| 67 | 2,4-$Br_2$ | " |  |
| 68 | 3-Cl, 4-O—⟨⟩—Cl | " |  |
| 69 | 2-Cl, 6-$OC_6H_5$ | " |  |
| 70 | 2-$CH(CH_3)_2$, 5-Cl | " |  |
| 71 | 2-$CH(CH_3)_2$, 4-Cl | " |  |
| 72 | 2-Cl, 3-$CF_3$, 4-F | " |  |
| 73 | 2,6-$Cl_2$ | " |  |
| 74 | 2-Cl, 4-$CH_3$ | " |  |
| 75 | 2-$OCH_3$, 4-$CH_3$ | " |  |
| 76 | 2-$CH_3$, 4-$OCH_3$ | " |  |
| 77 | 2,4-$(OCH_3)_2$ | " |  |
| 78 | 4-$OC_6H_5$ | " |  |
| 79 | 2,4-$(CH_3)_2$ | —$CH_3$ |  |
| 80 | 2,3-$(CH_3)_2$ | " |  |

TABLE 2-continued

R²=COOR³

| Example No. | (R¹)ₙ | R³ | m.p. (°C.) |
|---|---|---|---|
| 81 | 2-CH₃ | " | |
| 82 | 2,6-(C₂H₅)₂ | " | |
| 83 | 2-CH₃, 4-Cl | " | |
| 84 | 2,4-(CH₃)₂ | —C₃H₇ (i) | |
| 85 | 2,4-(CH₃)₂ | —C₄H₉ (n) | |
| 86 | 2,4-(CH₃)₂ | —C₅H₁₁ (n) | |
| 87 | 2,4-(CH₃)₂ | —C₂H₄OCH₃ | |
| 88 | 2,4-(CH₃)₂ | Cyclohexyl | |
| 89 | 2,4-(CH₃)₂ | Cyclopentyl | |
| 90 | 2,4-(CH₃)₂ | —C₈H₁₇ (n) | |
| 91 | 4-SC₆H₅ | —C₂H₅ | |
| 92 | 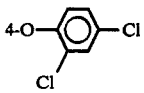 | —C₂H₅ | |

(B) EXAMPLES OF FORMULATION

An emulsifiable concentrate is obtained by dissolving 10 g of an active compound of formula I at room temperature in 100 cc of a mixture consisting of 85 parts by weight of dimethyl formamide, 3 parts by weight of nonylphenol polyglycol ether and 7 parts by weight of oxethylated castor oil. The concentrate can be readily emulsified by stirring into water.

(C) BIOLOGICAL EXAMPLES

The biological effect of the compounds of the formula I according to the invention is illustrated by the following Examples I and II in which the following products are used as comparative substances:

Compound A: Chloromethiuron
 [N¹-dimethyl-N²-(4-chloro-2-methylphenyl)-thiourea] (DE-OS No. 2,337,122)

Compound B: Clenpyrin
 [1-n-butyl-2-(3,4-dichlorophenylimino)-pyrrolidine] (Enders et al., Pestic. Sci. 4, pages 823 to 838 (1973))

EXAMPLE I

Test with ticks: inhibition of reproduction

The compounds listed in the following Table I are formulated as described in the formulation example and the emulsifiable concentrates are diluted with water to a concentration of 1,000 ppm. of active compound.

Each time 10 females of the species Boophilus microplus (tropical cattle tick) full with blood are dipped for 5 minutes into the respective active substance emulsion. They are then dried on filter paper and sticked with the dorsal side on an adhesive film. For ovulation the ticks are kept in a heating cabinet at 28° C. and high atmospheric humidity (80% of relative humidity).

To evaluate the effectiveness of the active substance formulations the following properties are determined:
 (a) inhibition of ovulation
 (b) size of the egg deposits
 (c) emergency rate of larvae The total damage expressed as inhibition of the reproduction capacity (or fertility) is calculated from the partial damages (a), (b), and (c). Consequently, a 100% inhibition of the reproduction capacity indicates that the ticks have no descendants and 0% means that they have normal descendants the number of which does not differ from that of untreated control animals.

The test results are listed in the following Table I. It can be seen that the compounds according to the invention are distinctly superior to the comparative substance.

TABLE I

| Compound (Example) | inhibition of reproduction capacity % | compound (Example) | inhibition of reproduction capacity % |
|---|---|---|---|
| 1 | 100 | 40 | 100 |
| 11 | 100 | 41 | 100 |
| 10 | 100 | 42 | 100 |
| 6 | 100 | 2 | 100 |
| 5 | 100 | 49 | 100 |
| 3 | 100 | 50 | 100 |
| 8 | >50 | 52 | 100 |
| 33 | 100 | 56 | 100 |
|  |  | 51 | 90 |
|  |  | 58 | 85 |
|  |  | 61 | 95 |
| comparative substance A | 50 | | |

EXAMPLE II

Detaching effect with ticks

PVC tubes (4 cm in diameter) provided with screw caps are fastened by means of adhesive tape to the depilated flanks of Guinea pigs. The limited skin areas are then infested with hungry ticks of the type Rhipicephalus sanguineus. 72 hours after infestation the ticks are completely wetted with aqueous emulsions of the active compounds according to the invention and of comparative compounds A and B, which emulsions contain 50 ppm of the compounds to be tested. 4 Hours after the treatment the detaching effect is evaluated (cf. Gladney et al., J. Med. Entom. 11, pages 369-372 (1974)).

The test results are summarized in Table II.

| Compound (Example) | detaching effect (%) | compound (Example) | detaching effect (%) |
|---|---|---|---|
| 1 | 100 | 39 | 100 |
| 5 | 70 | 40 | 100 |
| 33 | 100 | 41 | 100 |
| A (comp.) | 10 | | |
| B (comp.) | 40 | | |

What is claimed is:

1. Substituted N¹-vinyl-N¹-methyl-N²-aryl-formamidines of the formula I $$(R^1)_n-\text{C}_6\text{H}_{5-n}-N=CH-\underset{\underset{CH_3}{|}}{N}-CH-C\underset{COOR^3}{\overset{R^2}{\diagup}} \quad (I)$$

in which
 n is zero or a number from 1 to 3,
 R¹ is halogen, (C₁-C₄)-alkyl, (C₁-C₄)-alkoxy, (C₁-C₄)-alkylthio, trifluormethyl, nitro, cyano, phenoxy, halophenoxy, phenylthio, or halophenylthio, in the case of n being 2 or 3 the radicals R¹ possibly being identical or different,
 R² is —CN or —COOR³ and
 R³ is (C₁-C₈)-alkyl, (C₁-C₈)-alkoxyalkyl or (C₃-C₆)-cycloalkyl.

2. Pesticidal composition containing an effective amount of a compound of the formula I as claimed in claim 1 as active substance and a carrier therefor.

3. Pesticidal composition as claimed in claim 2, containing from 2 to 95% by weight, preferably 10 to 60% by weight, of a compound as claimed in claim 1 as active substance and formulation auxiliaries therefor as a carrier vehicle.

4. Method of combating insects and acaridae, which comprises applying an effective amount of a compound as claimed in claim 1 to a locus infected with insects or acaridae.

5. A compound as claimed in claim 1, wherein $(R^1)_n$ is dimethyl.

6. A compound as claimed in claim 1 having the formula

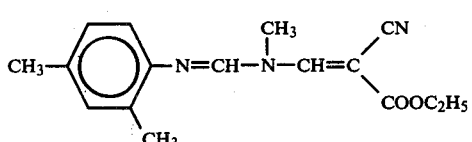

7. A compound as claimed in claim 1 having the formula

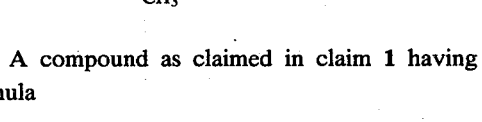

8. A compound as claimed in claim 1 having the formula

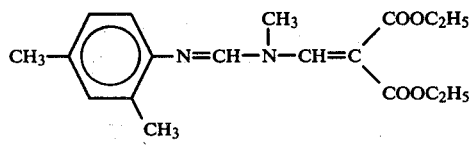

9. A compound as claimed in claim 1 having the formula

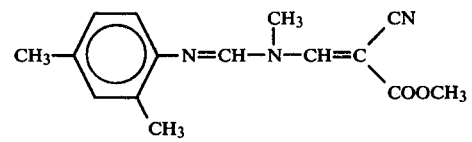

10. A compound as claimed in claim 1 having the formula

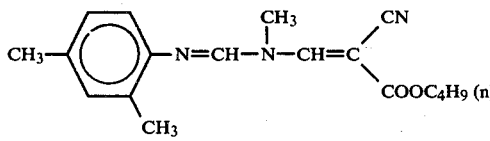

11. A compound as claimed in claim 1 having the formula

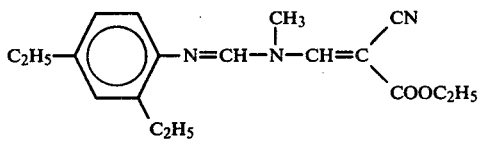

12. A compound as claimed in claim 1 having the formula

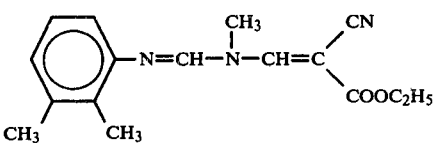

13. A compound as claimed in claim 1 having the formula

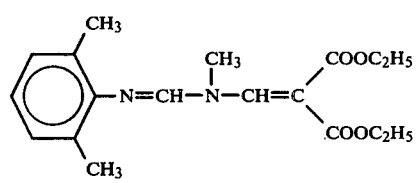

14. A compound as claimed in claim 1 having the formula

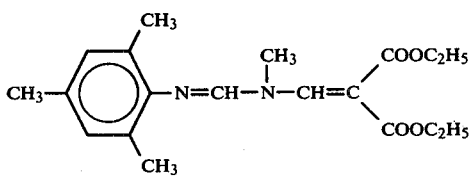

15. A compound as claimed in claim 1 having the formula

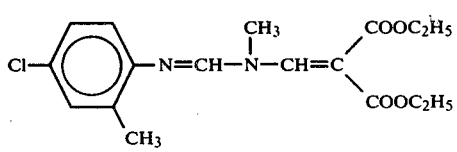

* * * * *